United States Patent
Carter

(10) Patent No.: US 9,095,708 B2
(45) Date of Patent: Aug. 4, 2015

(54) TRANSITIONING OPERATING MODES IN A MEDICAL PROSTHESIS

(71) Applicant: Cochlear Limited, Sydney (AU)

(72) Inventor: Paul Carter, Sydney (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/917,862

(22) Filed: Jun. 14, 2013

(65) Prior Publication Data

US 2014/0270285 A1    Sep. 18, 2014

Related U.S. Application Data

(60) Provisional application No. 61/791,538, filed on Mar. 15, 2013.

(51) Int. Cl.
  *H04R 25/00* (2006.01)
  *A61N 1/36* (2006.01)
  *H04R 29/00* (2006.01)

(52) U.S. Cl.
  CPC ............ *A61N 1/36032* (2013.01); *H04R 25/70* (2013.01)

(58) Field of Classification Search
  USPC ............... 381/60, 312–321, 94.1, 94.2, 94.7, 381/94.8, 101, 102, 103, 104, 107; 607/55–57, 60, 62, 131; 704/271, 233
  See application file for complete search history.

(56) References Cited

U.S. PATENT DOCUMENTS

| | | | | |
|---|---|---|---|---|
| 6,175,634 | B1 * | 1/2001 | Graumann | 381/94.1 |
| 6,205,360 | B1 * | 3/2001 | Carter et al. | 607/57 |
| 7,181,033 | B2 * | 2/2007 | Fischer et al. | 381/317 |
| 7,609,841 | B2 | 10/2009 | Freed | |
| 7,653,205 | B2 * | 1/2010 | Baumann et al. | 381/313 |
| 7,995,781 | B2 | 8/2011 | Baumann | |
| 8,054,999 | B2 * | 11/2011 | Rasmussen | 381/312 |
| 2007/0140512 | A1 * | 6/2007 | Hain et al. | 381/106 |
| 2011/0249839 | A1 * | 10/2011 | Mindlin et al. | 381/314 |

* cited by examiner

*Primary Examiner* — Curtis Kuntz
*Assistant Examiner* — Sunita Joshi
(74) *Attorney, Agent, or Firm* — McDonnell Boehnen Hulbert & Berghoff LLP

(57) ABSTRACT

The present disclosure describes systems and methods to transition a hearing prosthesis between different stimulation strategies. In accordance with one embodiment, a method is provided and includes operating a hearing prosthesis in accordance with a first parameter, receiving an instruction to operate the hearing prosthesis in accordance with a second parameter, and in response to the receiving, transitioning to operate the hearing prosthesis in accordance with the second parameter by operating the hearing prosthesis in accordance with at least one intermediate parameter. In accordance with another embodiment, the method includes transitioning to operate the hearing prosthesis in accordance with a third operation strategy characterized by alternating between periods of (i) operating in accordance with the first operation strategy, and (ii) operating in accordance with the second operation strategy, and increasing an amount of time in which the hearing prosthesis is operating in accordance with the second operation strategy.

14 Claims, 10 Drawing Sheets

TRANSITIONING OPERATING MODES IN A MEDICAL PROSTHESIS

BACKGROUND

Various types of hearing prostheses may provide persons having different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea, where sound vibrations are converted into neural signals, or any other part of the ear, auditory nerve, or brain that is associated with and/or processes the neural signals.

Persons with some forms of conductive hearing loss may benefit from hearing prostheses such as acoustic hearing aids or vibration-based hearing devices. An acoustic hearing aid typically includes a small microphone to detect sound, an amplifier to amplify certain portions of the detected sound, and a small speaker to transmit the amplified sounds into the person's ear. Vibration-based hearing devices typically include a small microphone to detect sound and a vibration mechanism to apply vibrations corresponding to the detected sound to a person's bone, thereby causing vibrations in the person's inner ear, thus bypassing the person's auditory canal and middle ear. Vibration-based hearing devices may include bone-anchored hearing devices, direct acoustic cochlear stimulation devices, or other vibration-based devices. A bone-anchored hearing device typically utilizes a surgically-implanted mechanism to transmit sound via direct vibrations of the skull. Similarly, a direct acoustic cochlear stimulation device typically utilizes a surgically-implanted mechanism to transmit sound via vibrations corresponding to sound waves to generate fluid motion in a person's inner ear. Other non-surgical vibration-based hearing devices may use similar vibration mechanisms to transmit sound via direct vibration of teeth or other cranial or facial bones.

Persons with certain forms of sensorineural hearing loss may benefit from hearing prostheses such as cochlear implants and/or auditory brainstem implants. For example, cochlear implants may provide a person having sensorineural hearing loss with the ability to perceive sound by stimulating the person's auditory nerve via an array of electrodes implanted in the person's cochlea. The cochlear implant detects sound waves and converts them into a series of electrical stimulation signals that are delivered to the implant recipient's cochlea via the array of electrodes. Auditory brainstem implants may use technology similar to cochlear implants, but instead of applying electrical stimulation to a person's cochlea, an auditory brainstem implant applies electrical stimulation directly to a person's brain stem, bypassing the cochlea altogether. Electrically stimulating auditory nerves in a cochlea with a cochlear implant or electrically stimulating a brainstem may enable a person with sensorineural hearing loss to perceive sound.

Typically, at one or more times during the life of a hearing prosthesis, an audiologist or other professional configures or reconfigures the prosthesis with a particular set of operating parameters. Generally, these operating parameters are specially tailored to address the recipient's particular type of hearing loss. However, some recipients are hesitant to accept any new operating parameters because of potential discomfort experienced as a result of the new way in which the hearing prosthesis applies stimulation. Accordingly, it may be advantageous to mitigate this potential discomfort.

SUMMARY

The present description sets forth systems and methods to facilitate a hearing prosthesis transitioning between different stimulation strategies or parameters of a stimulation strategy. It is recognized that the discomfort experienced by a hearing prosthesis recipient as a result of the prosthesis engaging in a new stimulation strategy may be associated with the recipient having to re-learn how to hear with the new stimulation strategy. In accordance with this recognition, one mitigating solution involves transitioning between two stimulation strategies by incorporating at least one intermediate parameter over an extended duration of time. A further description of this, and other solutions, is provided herein.

In accordance with at least some embodiments of the present disclosure, a method is provided and includes a sound processor operating a hearing prosthesis in accordance with a first parameter, the sound processor receiving an instruction to operate the hearing prosthesis in accordance with a second parameter, and in response to the receiving, the sound processor transitioning to operate the hearing prosthesis in accordance with the second parameter by operating the hearing prosthesis in accordance with at least one intermediate parameter.

In accordance with another embodiment, another method is provided and includes a sound processor operating a hearing prosthesis in accordance with a first operation strategy, the sound processor receiving an instruction to operate the hearing prosthesis in accordance with a second operation strategy, in response to the receiving, the sound processor transitioning to operate the hearing prosthesis in accordance with a third operation strategy characterized by the sound processor alternating between periods of (i) operating the hearing prosthesis in accordance with the first operation strategy, and (ii) operating the hearing prosthesis in accordance with the second operation strategy, and the sound processor increasing an amount of time in which the sound processor is operating the hearing prosthesis in accordance with the second operation strategy.

In accordance with another embodiment, another method is provided and includes a sound processor operating a hearing prosthesis in accordance with a first operation strategy, the sound processor receiving an instruction to operate the hearing prosthesis in accordance with a second operation strategy, in response to the receiving, the sound processor transitioning to operate the hearing prosthesis in accordance with a third operation strategy characterized by the sound processor alternating between periods of (i) operating the hearing prosthesis in accordance with the first operation strategy, and (ii) operating the hearing prosthesis in accordance with the second operation strategy, the sound processor increasing a loudness associated with the second operation strategy, and the sound processor decreasing a loudness associated with the first operation strategy.

DETAILED DESCRIPTION

The following detailed description sets forth various features and functions of the disclosed systems and methods with reference to the accompanying figures. In the figures, similar symbols identify similar components, unless context dictates otherwise. The illustrative system and method embodiments described herein are not meant to be limiting. Certain aspects of the disclosed systems and methods can be arranged and combined in a wide variety of different configurations, all of which are contemplated herein.

Certain aspects of the disclosed systems, methods, and articles of manufacture are described herein with reference to hearing prosthesis embodiments and, more particularly, cochlear implant embodiments. However, the disclosed systems, methods, and articles of manufacture are not so limited. Many of the disclosed features and functions described with respect to the cochlear implant embodiments may be equally applicable to other embodiments that may include other types of medical stimulation prostheses, such as vibration-based hearing devices, direct acoustic stimulation devices, auditory brain stem implants, or any other type of medical stimulation prosthesis, such as a prosthetic-limb stimulation device, that employs a particular stimulation strategy or a number of changeable stimulation parameters.

Figure 1:
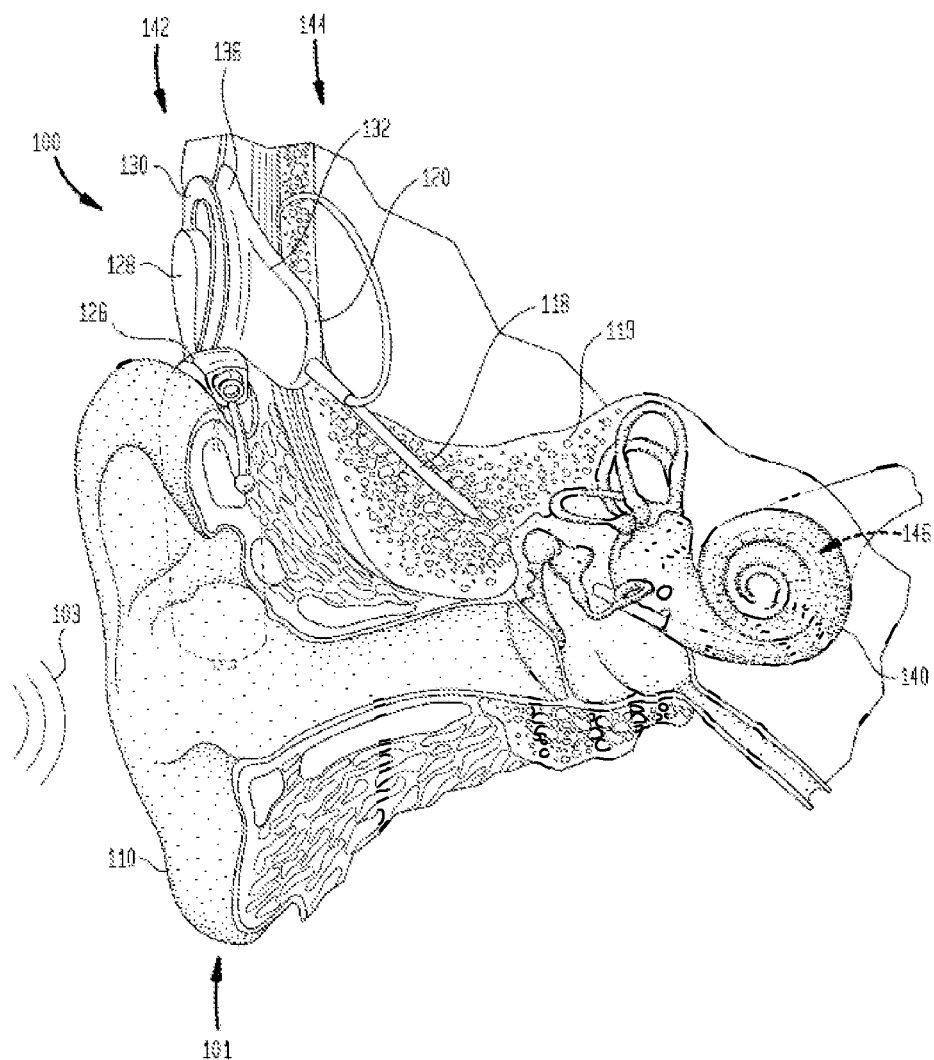
FIG. 1 depicts an example hearing prosthesis arrangement.

FIG. 1 is a perspective view of an example implanted hearing prosthesis (cochlear implant system 100) to assist a recipient in perceiving sound waves 103. Cochlear implant system 100 includes an external component 142 and an internal component 144. The internal component has an internal receiver/transceiver unit 132, a stimulator unit 120, and an elongated stimulating assembly 118. The internal receiver/transceiver unit 132 permits the cochlear implant system 100 to receive and/or transmit signals to an external device 126 and includes an internal coil 136, and preferably, a magnet (not shown) fixed relative to the internal coil 136 to align with a magnet 128 on the external component 142. Internal receiver unit 132 and stimulator unit 120 are hermetically sealed within a biocompatible housing, sometimes collectively referred to as a stimulator/receiver unit. The magnets facilitate the operational alignment of the external and internal coils, enabling internal coil 136 to receive power and stimulation data from external coil 130. Elongate stimulating assembly 118 has a proximal end connected to stimulator unit 120, and a distal end with an electrode array 146 implanted in cochlea 140. Stimulating assembly 118 extends from stimulator unit 120 to cochlea 140 through mastoid bone 119.

External coil 130 transmits electrical signals (e.g., power and stimulation data) to internal coil 136 via a radio frequency (RF) link, as noted above. Internal coil 136 is a wire antenna coil comprised of multiple turns of electrically insulated single-strand or multi-strand platinum or gold wire, for example. The electrical insulation of internal coil 136 is provided by a flexible silicone molding (not shown). In use, implantable receiver unit 132 may be positioned in a recess of the temporal bone adjacent auricle 110 of the recipient. Various types of energy transfer, such as infrared (IR), electromagnetic, capacitive and inductive transfer, may be used to transfer the power and/or data from external device to cochlear implant.

Figure 2:
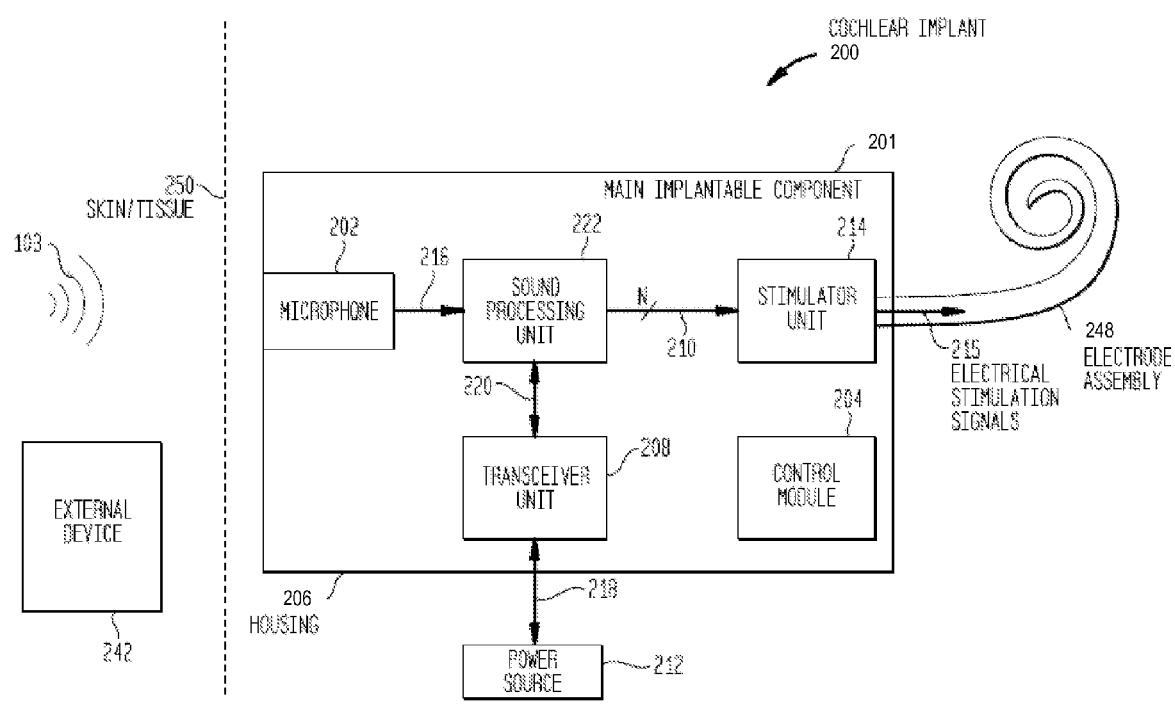
FIG. 2 is a block diagram depicting certain selected hearing prosthesis components of an example hearing prosthesis.

FIG. 2 is a functional block diagram of a cochlear implant system 200 that is totally implantable. That is, all components of cochlear implant system 200 are configured to be implanted under skin/tissue 250 of a recipient. As a result, cochlear implant system 200 operates, for at least a finite period of time, without the need of an external device. An external device 242 can be used to charge the internal battery, to supplement the performance of the implanted microphone/ system, or to serve as an external battery when the internal battery has exceeded its useful lifetime and no longer functions. External device 242 may include or comprise a dedicated charger or a conventional cochlear implant sound processor, for example.

As shown, cochlear implant system 200 includes a main implantable component 201 having a hermetically sealed, biocompatible housing 206. Disposed in main implantable component 201 is a microphone 202 configured to sense a sound signal 103. Microphone 202 preferably includes one or more components to pre-process the microphone output. As an alternative, the microphone and other aspects of the system can be included in a tethered module as opposed to in a unitary body as shown in FIG. 2.

In operation, an electrical signal 216 representing sound signal 103 detected by microphone 202 is provided from the microphone to sound processing unit 222. Sound processing unit 222 implements one or more speech processing and/or sound coding strategies to convert the pre-processed microphone output into data signals 210 for use by stimulator unit 214. Stimulator unit 214 utilizes data signals 210 to generate electrical stimulation signals 215 for delivery to the cochlea of the recipient. In the example depicted in FIG. 2, cochlear implant system 200 comprises a stimulating electrode assembly 248 for delivering stimulation signals 215 to the cochlea.

As further shown, cochlear implant system 200 also includes a power source 212 comprising, for example, one or more rechargeable batteries. As described below, power is stored in power source 212, which can be recharged by external device 242. The power may then be distributed to the other components of cochlear implant system 200 as needed for operation.

Main implantable component 201 further includes a control module 204. Control module 204 includes various components for controlling the operation of cochlear implant 200, or for controlling specific components of cochlear implant system 200. For example, control module 204 controls the delivery of power from power source 212 to other components of cochlear implant system 200. Main implantable component 201 and power source 212 are shown as separate components. However, power source 212 may alternatively be integrated into hermetically sealed housing 206 or part of a separate module coupled to component 200.

As further shown, cochlear implant system 200 also includes a transceiver unit 208 that permits cochlear implant system 200 to receive and/or transmit signals to another device. Cochlear implant system 200 is shown having a transceiver unit 208 inside the main implantable component 201. However, in alternative arrangements, cochlear implant system 200 includes a transceiver unit that is implanted elsewhere in the recipient outside of main implantable component 201.

In the example depicted, transceiver unit 208 is configured to transcutaneously receive power and/or data from external device 242. Transceiver unit 208 includes a collection of one or more implanted components that form part of a transcutaneous energy transfer system. For example, transceiver unit 208 includes components that receive and/or transmit data or power, such as a coil for a magnetic inductive arrangement, an antenna for an alternative RF system, capacitive plates, or any other suitable arrangement. Various types of energy transfer, such as infrared (IR), electromagnetic, capacitive, and inductive transfer, can be used to transfer the power and/or data from external device 242 to other parts of the cochlear implant system 200.

In the illustrative arrangement of FIG. 2, external device 242 comprises a power source (not shown) disposed in a Behind-The-Ear (BTE) unit. External device 242 also includes components of a transcutaneous energy transfer link formed with transceiver unit 208 to transfer the power and/or data to cochlear implant system 200. The external device 242 shown in FIG. 2 is merely illustrative, and other external devices can be alternatively used.

As mentioned above, during operation, the sound processing unit 222 generates data signals 210 based on the microphone 202 output. These data signals 210 identify to the stimulator unit 214 at least two electrodes from the electrode assembly 248 between which an electrical signal is applied. Additionally, these data signals also identify an amplitude of the electrical signal to apply to the indicated electrodes.

The sound processing unit 222 generates these data signals 210 in accordance with a particular sound coding strategy (or, more generally, a stimulation strategy or an operation strategy). Generally, a stimulation strategy is a set of rules that define how the sound processing unit 222 analyzes the microphone 202 output and generates data signals 210. More particularly, a stimulation strategy specifies various operating parameters with which the hearing prosthesis operates. In cochlear implants, for example, a stimulation strategy dictates the specific electrodes to which the stimulator unit should apply electrical signals, a maximum amplitude (referred to as comfort level) and minimum amplitude (referred to as threshold level) of the electrical signals with which to stimulate those electrodes, and the order and configuration in which to apply the electrical signals. In operation, hearing prosthesis 200 is configured to use a variety of stimulation strategies, including, for instance, Continuous Interleaved Sampling (CIS), Spectral Peak (SPEAK), Advanced Combination Encoder (ACE), or any other suitable standard or proprietary stimulation strategy now known or later developed.

In some situations it is advantageous for a hearing prosthesis to change all or part of a stimulation strategy. For example, from time to time, an audiologist may recommend adjustment of certain parameters of a recipient's stimulation strategy, such as increasing or decreasing a recipient's comfort level. Alternatively, a recipient may invoke a change to a more suitable stimulation strategy in anticipation of entering a different sound environment, such as a noisy restaurant or a concert. Other reasons for changing all or part of a stimulation strategy are possible as well.

Disclosed herein are several embodiments that facilitate a comfortable transition between different operating parameters of a stimulation strategy, or between different stimulation strategies altogether. In accordance with one general embodiment, a hearing prosthesis engages in a relatively slow transition from one stimulation strategy to another stimulation strategy, rather than engaging in an immediate transition. Depending on the particular embodiment, the transition occurs over the span of several seconds, hours, or weeks. In some embodiments, the transition occurs according to a linear function while in other embodiments, the transition occurs according to some other type of function, such as a logarithmic function or other scaled decay or growth function. By transitioning a hearing prosthesis in this manner, a recipient is less likely to experience an uncomfortable transition. The gradual transition between stimulation strategies therefore results in a better user experience.

Figure 3:
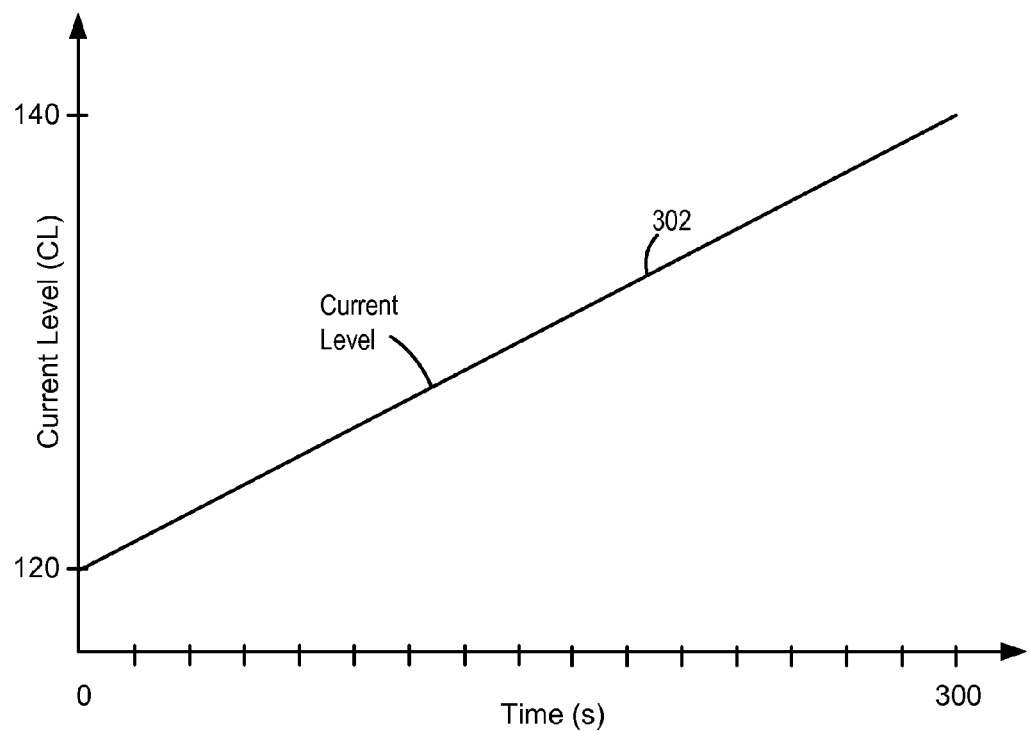
FIG. 3 depicts a graph illustrating an example transition, in accordance with one embodiment.

FIG. 3 depicts a graph illustrating an example transition of the comfort level parameter, in accordance with one embodiment. As shown, a hearing prosthesis, such as hearing prosthesis 200, transitions from operating with a comfort level of 120 CL to operating with a comfort level of 140 CL. Generally, CL (or Current Level) is a unit of electric current that is logarithmically related to the absolute current. However, rather than immediately transitioning from 120 CL to 140 CL, the hearing prosthesis slowly transitions from 120 CL to 140 CL over the span of several hundred seconds. In the embodiment depicted, the transition between the 120 CL comfort level and the 140 CL comfort level occurs according to linear function 302 over a span of 300 seconds. At 0 seconds, the hearing prosthesis operates with a comfort level of about 120 CL; about 20 seconds later the hearing prosthesis operates with a comfort level of about 121.33 CL; and at another 20 seconds later, the hearing prosthesis operates with a comfort level of about 122.66 CL. In the embodiment depicted, the transition occurs in this linear manner until at about 300 seconds, at which time the hearing prosthesis operates with a comfort level of about 140 CL.

Figure 4:
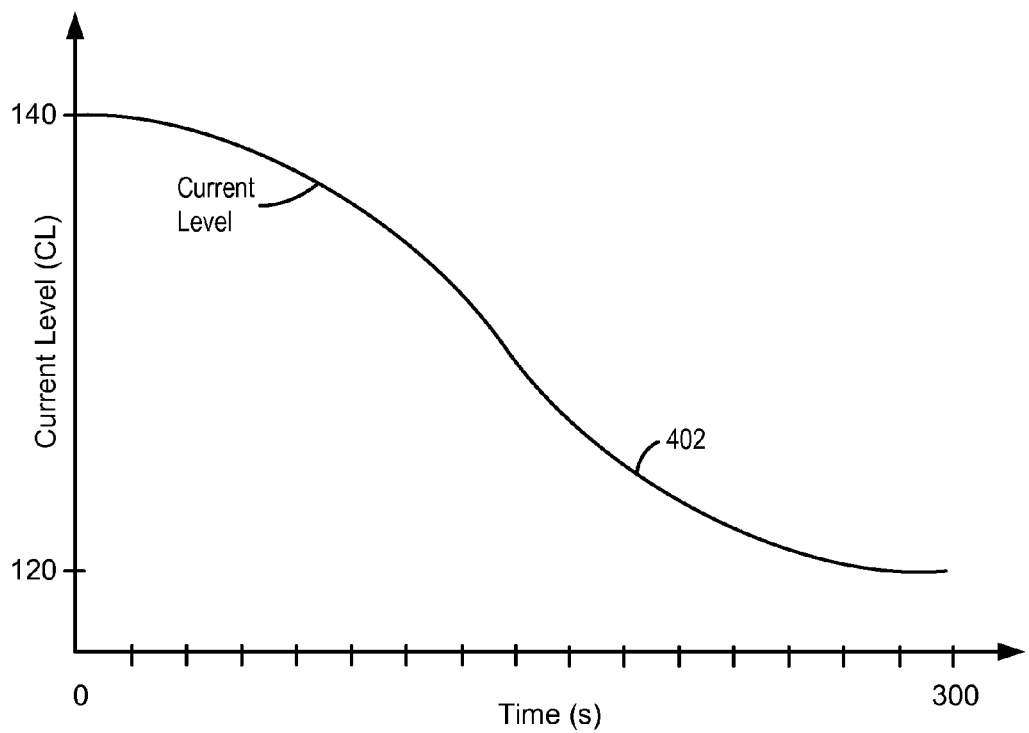
FIG. 4 depicts a graph illustrating an example transition, in accordance with one embodiment.

FIG. 4 depicts another graph illustrating an example transition of the comfort level parameter, in accordance with one embodiment. As shown, a hearing prosthesis, such as hearing prosthesis 200, transitions from operating with a comfort level of 140 CL to operating with a comfort level of 120 CL. Similar to the embodiment depicted in FIG. 3, in the embodiment depicted in FIG. 4, rather than immediately transitioning from 140 CL to 120 CL, the hearing prosthesis slowly transitions from 140 CL to 120 CL over a span of 300 seconds. However, in the embodiment depicted in FIG. 4, the transition occurs according to a non-linear function 402, rather than a linear function. Thus, at 0 seconds, the hearing prosthesis operates with a comfort level of about 140 CL; about 20 seconds later the hearing prosthesis operates with a comfort level of about 139 CL; and at about another 130 seconds later, the hearing prosthesis operates with a comfort level of about 130 CL. In the embodiment depicted, the transition occurs in this non-linear manner until at about 300 seconds, at which time the hearing prosthesis operates with a comfort level of about 120 CL.

The embodiments depicted in FIGS. 3 and 4 are examples. In other embodiments, for instance, the hearing prosthesis transitions between different stimulation strategies (or different parameters of stimulation strategies) in accordance with other types of functions and over durations shorter or longer than 300 seconds.

In accordance with another general embodiment, a hearing prosthesis engages in a progressive transition between stimulation strategies (or parameters of a stimulation strategy) in accordance with a time-varying function. In such embodiments, the hearing prosthesis switches or alternates between an initial stimulation strategy and a target stimulation strategy for a period of time during which the transition occurs between stimulation strategies (or parameters of a stimulation strategy). The hearing prosthesis gradually increases the time in which it operates in accordance with the target stimulation strategy. As a result of transitioning in this manner, a recipient may be less likely to experience an uncomfortable transition between discrete parameters of a stimulation strategy. Accordingly, a time-varying transition results in a better user experience.

Figure 5:
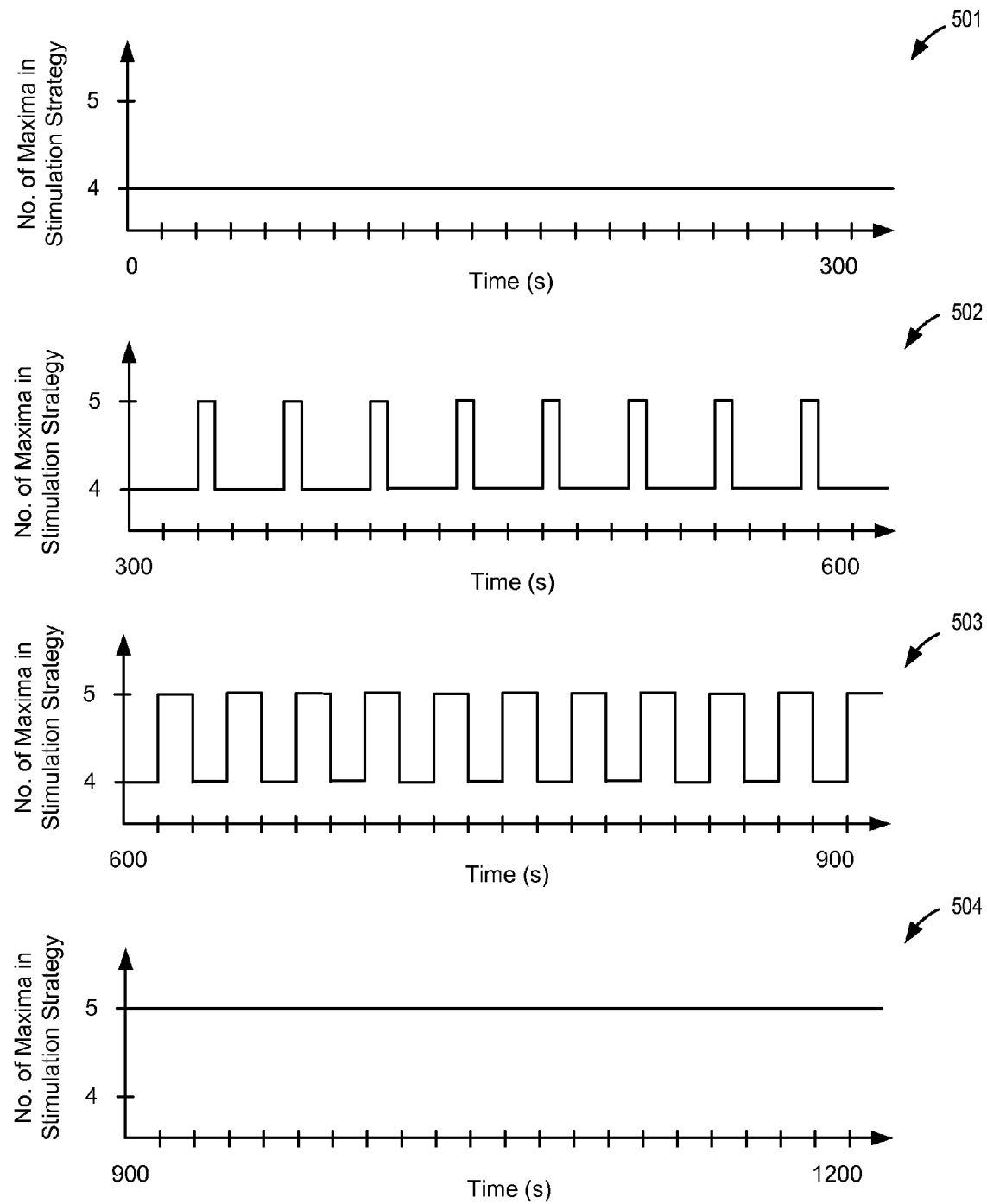
FIG. 5 depicts several graphs, which collectively illustrate an example transition, in accordance with one embodiment.

FIG. 5 depicts four graphs 501, 502, 503, and 504, which illustrate an example progressive transition from an initial stimulation strategy that features the use of four maxima to a target stimulation strategy that features the use of five maxima. The number of maxima used in a stimulation strategy refers to the number of frequency bands that are selected to be transmitted to the recipient during every sweep of all frequency bands. The selected bands are normally those with the highest energy, hence the use of the term "maxima."

As depicted in graph 501, from 0 seconds to 300 seconds, the hearing prosthesis operates according to the initial stimulation strategy. As depicted in graph 502, from 300 seconds to 600 seconds, the hearing prosthesis switches between operating according to the initial stimulation strategy and operating according to the target stimulation strategy. This switching is done at a sufficiently fast rate such that the recipient is not aware of an abrupt transition from the initial stimulation strategy to the target stimulation strategy, for example at intervals of 20 ms or less. During the period depicted in graph 502, the hearing prosthesis operates according to the initial stimulation strategy for about half as much time as it operates according to the target stimulation strategy. Moreover, during the duration depicted in graph 502, the hearing prosthesis transitions between the stimulation strategies at substantially regular intervals.

For instance, starting at about 300 seconds and lasting for about 40 seconds, the hearing prosthesis operates according to the initial stimulation strategy. At 340 seconds, the hearing prosthesis transitions to the target stimulation strategy and operates according thereto for about 20 seconds. And at about 360 seconds, the hearing prosthesis transitions back to operating according to the initial stimulation strategy. It will be appreciated that the transitions shown in FIG. 5, although depicted at discrete points in time such as 240 seconds, happen smoothly. In the embodiment depicted, the switching continues in this manner until about 600 seconds, at which time the hearing prosthesis increases the relative amount of time it spends operating according to the target stimulation strategy. When the hearing prosthesis increases the amount of time it spends operating according to the target stimulation strategy, it also decreases the amount of time it spends operating according to the initial stimulation strategy. As depicted in graph 503 for instance, the hearing prosthesis operates according to each stimulation strategy for about equal time periods (e.g., about 30 seconds). Moreover, as depicted, the hearing prosthesis switches between the two stimulation strategies at substantially regular intervals. In the embodiment depicted, the switching continues in this manner until about 900 seconds, at which time the hearing prosthesis stops switching back to the initial stimulation strategy and operates entirely according to the target stimulation strategy. This operation is depicted in graph 504.

The embodiment depicted by graphs 501, 502, 503, and 504 of FIG. 5 is an example. In other embodiments, the hearing prosthesis transitions between different stimulation strategies in other manners. For instance, in other embodiments, the hearing prosthesis incorporates more or fewer increases in the amount of time it spends operating according to the target stimulation strategy. In still other embodiments, the hearing prosthesis spends more or less time than 300 seconds engaging in each round of cycling before increasing the relative amount of time it spends operating according to the target stimulation strategy.

In some embodiments, a hearing prosthesis transitions between stimulation strategies using one or more intermediate parameters. For example, for an initial stimulation strategy that features four maxima and a target stimulation strategy that features six maxima, the hearing prosthesis engages in a progressive transition from the initial stimulation strategy to an intermediate strategy (e.g., a stimulation strategy that features five maxima), in accordance with the above-described process. Subsequently, the hearing prosthesis engages in a progressive transition from the intermediate stimulation strategy to the target stimulation strategy, in accordance with the above-described process.

In an alternative embodiment, during a period in which the hearing prosthesis switches between the initial stimulation strategy and the target stimulation strategy, rather than cycling between the stimulation strategies at regular intervals, the hearing prosthesis switches between the stimulation strategies at irregular intervals but maintains approximately the same relative ratio of time spent operating according to each strategy.

Figure 6:
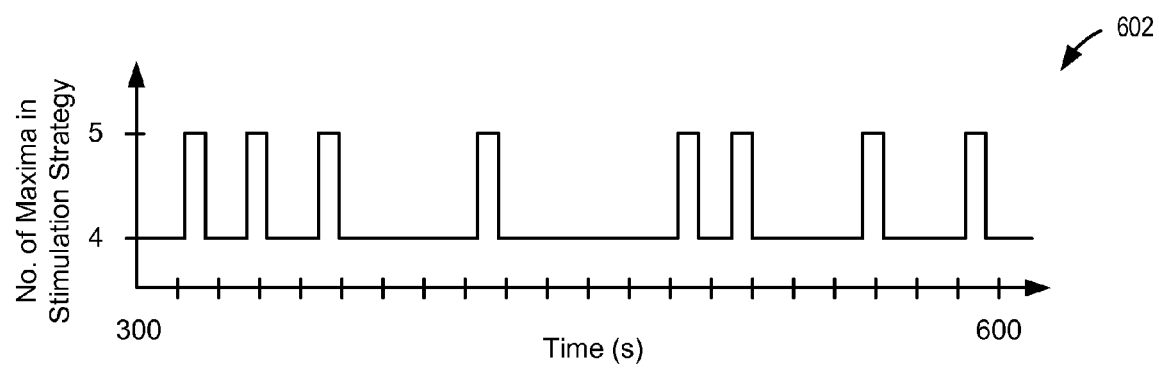
FIG. 6 depicts a graph illustrating an example transition, in accordance with one embodiment.

FIG. 6 depicts a graph 602 that illustrates an example of such an embodiment. As depicted, the hearing prosthesis transitions from the initial stimulation strategy (four maxima) to the target stimulation strategy (five maxima) at irregular, and perhaps random, intervals. In one embodiment, during such a transition, the switching time between strategies is chosen to be short enough so that the change is not perceptible to the user. During the period from 300 seconds to 600 seconds as depicted by the graph 602, the hearing prosthesis maintains the same relative ratio of time spent operating according to each strategy as during the time period depicted in graph 502 of FIG. 5. Cycling between the stimulation strategies at irregular intervals is referred to herein as adding "jitter" to the progressive transition process. In some embodiments, adding jitter to the transition process reduces the occurrence of buzzing effects that might otherwise be perceived by recipients during the transitions.

In another general embodiment, a hearing prosthesis engages in a transition between stimulation strategies (or parameters of a stimulation strategy) in accordance with a loudness-varying function. In such embodiments, the hearing prosthesis switches between an initial stimulation strategy and a target stimulation strategy while, at the same time, both increasing a loudness (or volume level) associated with the target stimulation strategy and decreasing a loudness associated with the initial stimulation strategy. By transitioning the hearing prosthesis in this manner, a recipient may be less likely to experience buzzing percepts during transition. Therefore, a loudness-varying transition may result in a better user experience.

Figure 7:
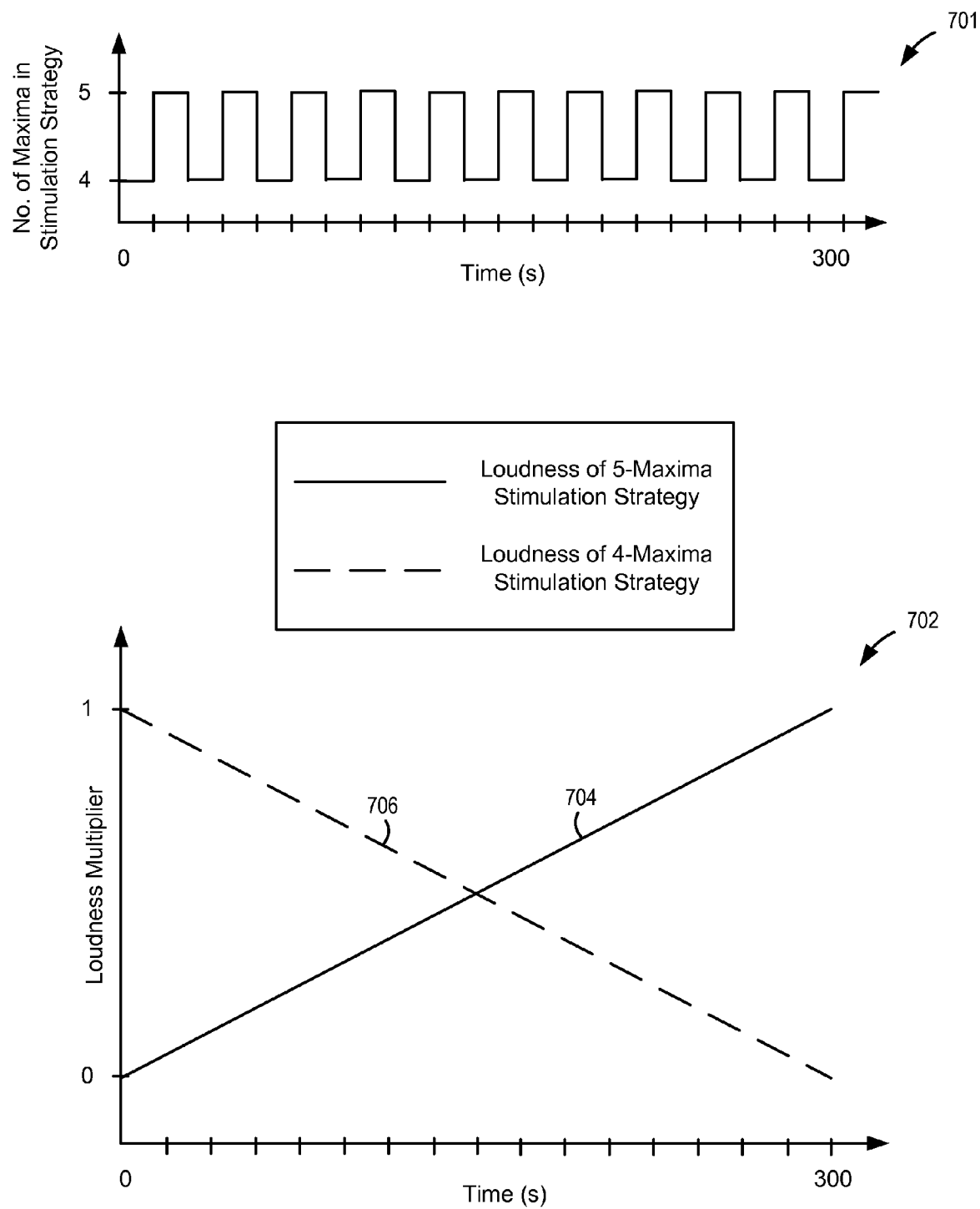
FIG. 7 depicts two graphs, which collectively illustrate an example transition, in accordance with one embodiment.

FIG. 7 depicts two graphs 701 and 702, which illustrate an example of a loudness-varying transition that takes place over 300 seconds, from an initial stimulation strategy that features the use of four maxima to a target stimulation strategy that features the use of five maxima. As depicted in graph 701, over the course of 300 seconds, the hearing prosthesis switches between the initial stimulation strategy and the target stimulation strategy while maintaining about an equal ratio of relative time spent operating according to each stimulation strategy. In one embodiment, the time between switches is short (fast) enough so that the change is not perceptible to the recipient. As depicted by graph 702, over the course of the same 300 seconds, the hearing prosthesis increases the loudness associated with the target stimulation strategy from a multiplier of zero to a multiplier of 1, in accordance with linear function 704. And, over the course of the same 300 seconds, the hearing prosthesis decreases the loudness associated with the initial stimulation strategy from a multiplier of 1 to a multiplier of 0 in accordance with linear function 706. The resulting stimulation signal that is applied to the recipient has an overall loudness of 1 or is equal in loudness to either the initial or target strategy running alone. In practice, the loudness of the overall signal is achieved by adjusting the stimulation current levels of each strategy. In order to achieve this transition, a function other than the linear function 706 may be utilized, based on the particular current-loudness characteristics of the stimulation mechanisms in the hearing prosthesis being transitioned.

The embodiment depicted by graphs 701 and 702 of FIG. 7 is an example. In other embodiments, for instance, the hearing prosthesis transitions between different stimulation strategies in more or less time than 300 seconds, using linear or non-linear loudness-varying functions, varying the loudness between multipliers other than 0 and 1, cycling between the initial stimulation strategy and the target stimulation strategy at regular or irregular intervals, and maintaining the same or different ratios of relative time spent operating according to each stimulation strategy.

In an alternative embodiment, for instance, a hearing prosthesis engages in a combination of the progressive transition and the loudness-varying transition. In such an embodiment, the hearing prosthesis switches between operating according to the initial stimulation strategy and operating according to the target stimulation strategy and intermittently increases the relative amount of time it spends operating according to the target stimulation strategy. At the same time, the hearing prosthesis increases a loudness associated with the target stimulation strategy while decreasing a loudness associated with the initial stimulation strategy. Other combinations of the above-described embodiments are possible as well, as are variations of the individual metrics, time frames, and functions, which were used as examples.

Figure 8:
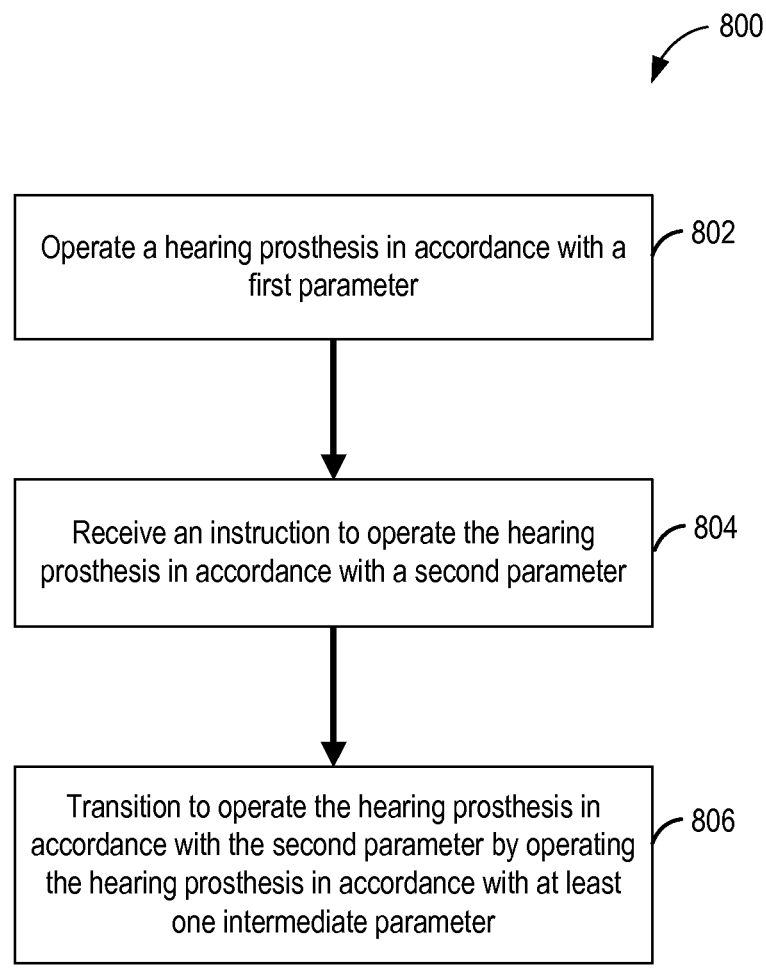
FIG. 8 depicts a flow chart, in accordance with one embodiment.

FIG. 8 is a flowchart 800 depicting an example method for transitioning between different parameters of stimulation strategies in a hearing prosthesis. The method depicted in FIG. 8 may be executed by one or more of the modules or sub-modules of hearing prosthesis 100 or hearing prosthesis 200, such as sound processing unit 222, stimulator unit 214, or control module 204. As depicted, the method begins at block 802 where a processor (e.g., sound processing unit 222) operates a hearing prosthesis (e.g., hearing prosthesis 200) in accordance with a first parameter. For example, the first parameter is a comfort level, such a comfort level of 120 CL. Other parameters with other values are possible as well.

At block 804, the processor receives an instruction to operate the hearing prosthesis in accordance with a second parameter. The entity or entities from which the instruction originates depends on the particular embodiment. For example, in one embodiment, the instruction originates from a device (e.g., a computing device) operated by an audiologist during a fitting session and is transmitted to hearing prosthesis 200 by way of external device 242 and/or a fitting system. In another embodiment, the instruction originates from a device operated by the recipient (e.g., by pressing a button on a behind-the-ear unit) and is transmitted to hearing prosthesis 200 via an external user interface. In still another embodiment, the instruction originates with the hearing prosthesis itself (e.g. in response to a change in received sound) and is transmitted to the sound processing unit 222 from another sub-module, such as the control module 204. Other examples are possible as well. Moreover, in one example, the second parameter is a comfort level, such as 140 CL; however, other parameters with other values are possible as well.

At block 806, the processor transitions to operate the hearing prosthesis in accordance with the second parameter by operating the hearing prosthesis in accordance with at least one intermediate parameter. In one embodiment for example, the hearing prosthesis transitions by operating the hearing prosthesis in accordance with several intermediate parameters in linear succession (e.g., 120 CL, 121 CL, 122 CL etc.). In other embodiments, other types of transitions are possible.

Figure 9:
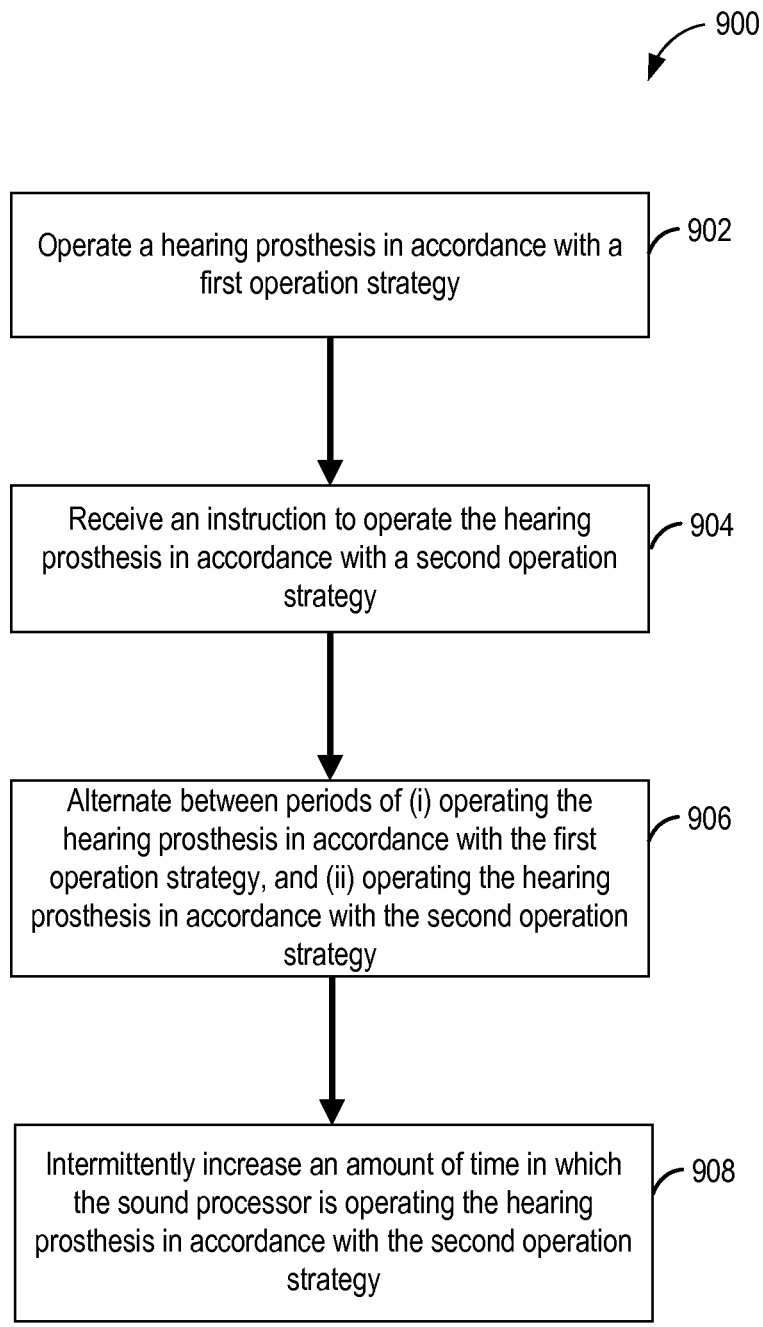
FIG. 9 depicts a flow chart, in accordance with one embodiment.

FIG. 9 is a flowchart 900 depicting an example method for transitioning between different operation strategies. The method depicted in FIG. 9 may be executed by one or more of the modules or sub-modules of hearing prosthesis 100 or hearing prosthesis 200, such as sound processing unit 222, stimulator unit 214, or control module 204. As depicted, the method begins at block 902, where a processor (e.g., sound processing unit 222) operates a hearing prosthesis (e.g., hearing prosthesis 200) in accordance with a first operation strategy. For example, the first operation strategy is a stimulation strategy that features the use of four maxima. However, other types of operation strategies are possible as well.

At block 904, the processor receives an instruction to operate the hearing prosthesis in accordance with a second operation strategy. Similar to block 804 of FIG. 8, this instruction may originate from a device (e.g., a computing device) operated by an audiologist, the recipient, or the hearing prosthesis itself and be appropriately transmitted to the hearing prosthesis. For example, the second operation strategy is a stimulation strategy that features the use of five maxima; however, other types of operation strategies are possible as well.

At block 906, the processor alternates between periods of (i) operating the hearing prosthesis in accordance with the first operation strategy and (ii) operating the hearing prosthesis in accordance with the second operation strategy. In one embodiment, the processor alternates between these two periods at regular intervals. However, in other embodiments, the processor alternates between these two periods at irregular intervals or random intervals.

At block 908, the processor increases (preferably intermittently) the amount of time in which the processor is operating the hearing prosthesis in accordance with the second operation strategy. In one embodiment, the processor increases the amount of time it operates the hearing prosthesis in accordance with the second operation strategy by also decreasing the amount of time it operates the hearing prosthesis in accordance with the first operating strategy. In some embodiments, the processor continues intermittently increasing this amount of time until the hearing prosthesis is operating exclusively in accordance with the second operation strategy. However, other ways of intermittently increasing this amount of time are possible as well.

Figure 10:
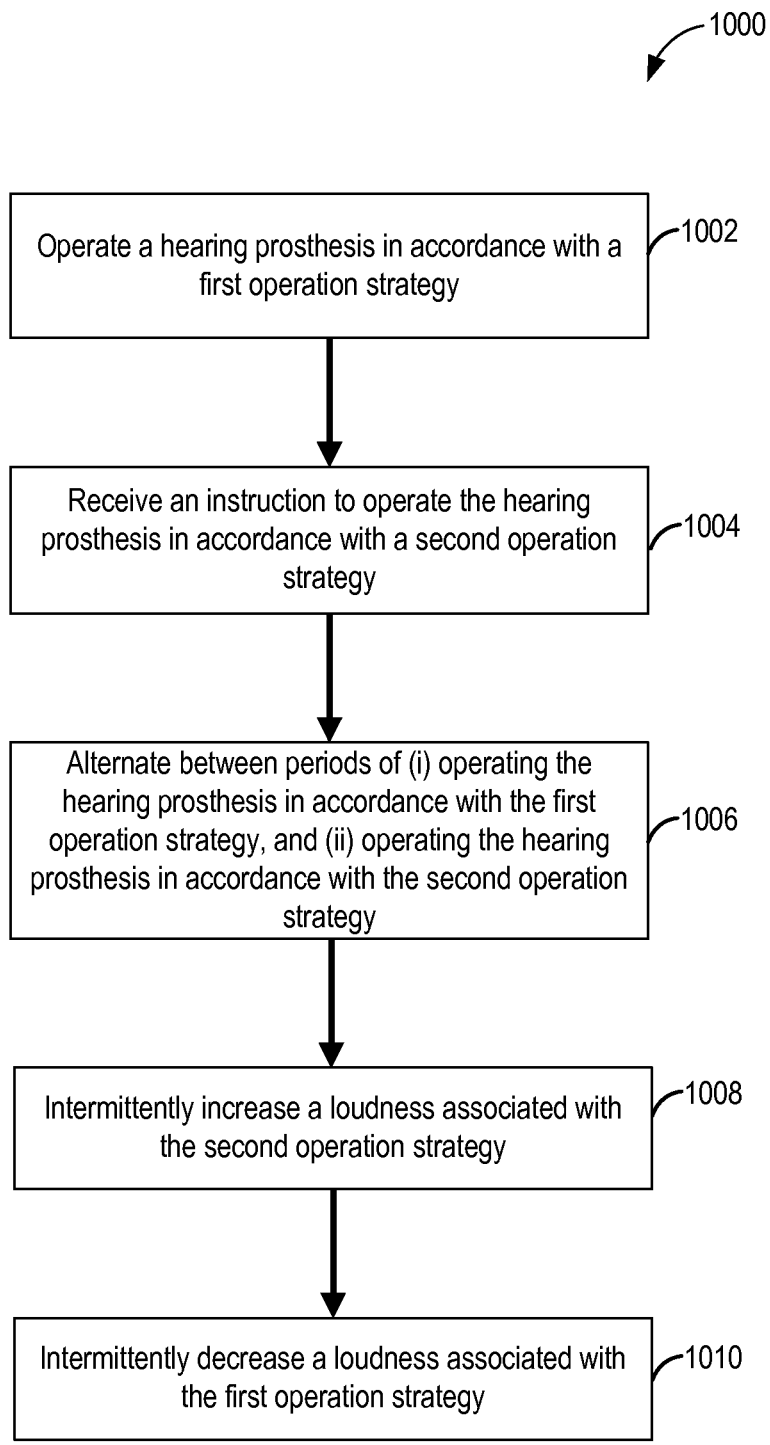
FIG. 10 depicts a flow chart, in accordance with one embodiment.

FIG. 10 is a flowchart 1000 depicting an example method for transitioning between different operation strategies. The method depicted in FIG. 10 may be executed by one or more of the modules or sub-modules of hearing prosthesis 100 or hearing prosthesis 200, such as sound processing unit 222, stimulator unit 214, or control module 204. As depicted, the method begins at block 1002, where a processor (e.g., sound processing unit 222) operates a hearing prosthesis (e.g., hearing prosthesis 200) in accordance with a first operation strategy. For example, the first operation strategy is a stimulation strategy that features the use of four maxima. However, other types of operation strategies are possible as well.

Similar to block 904 of FIG. 9, at block 1004, the processor receives an instruction to operate the hearing prosthesis in accordance with a second operation strategy. For instance, this instruction may originate from a device (e.g., a computing device) operated by an audiologist, the recipient, or the hearing prosthesis itself and be appropriately transmitted to the hearing prosthesis. For example, the second operation strategy is a stimulation strategy that features the use of five maxima. Other types of operation strategies are possible as well.

Similar to block 906 of FIG. 9, at block 1006, the processor alternates between periods of (i) operating the hearing prosthesis in accordance with the first operation strategy, and (ii) operating the hearing prosthesis in accordance with the second operation strategy. In one embodiment, the processor alternates between these two periods at regular intervals. However, in other embodiments, the processor alternates between these two periods at irregular intervals or random intervals.

At block 1008, the processor increases (preferably intermittently) a loudness associated with the second operation strategy. In one embodiment, the processor increases this loudness according to a linear function; however, in other embodiments, the processor increases this loudness in accordance with other types of functions.

Finally, at block 1010, the processor decreases (preferably intermittently) a loudness associated with the first operation strategy. Similar to block 1008, in one embodiment, the processor decreases this loudness according to a linear function; however, in other embodiments, the processor decreases this loudness in accordance with other types of functions.

In some embodiments, the disclosed features and functions of the systems, methods, and algorithms shown and described herein may be implemented as computer program instructions encoded on a computer readable medium in a machine-readable format.

Figure 11:
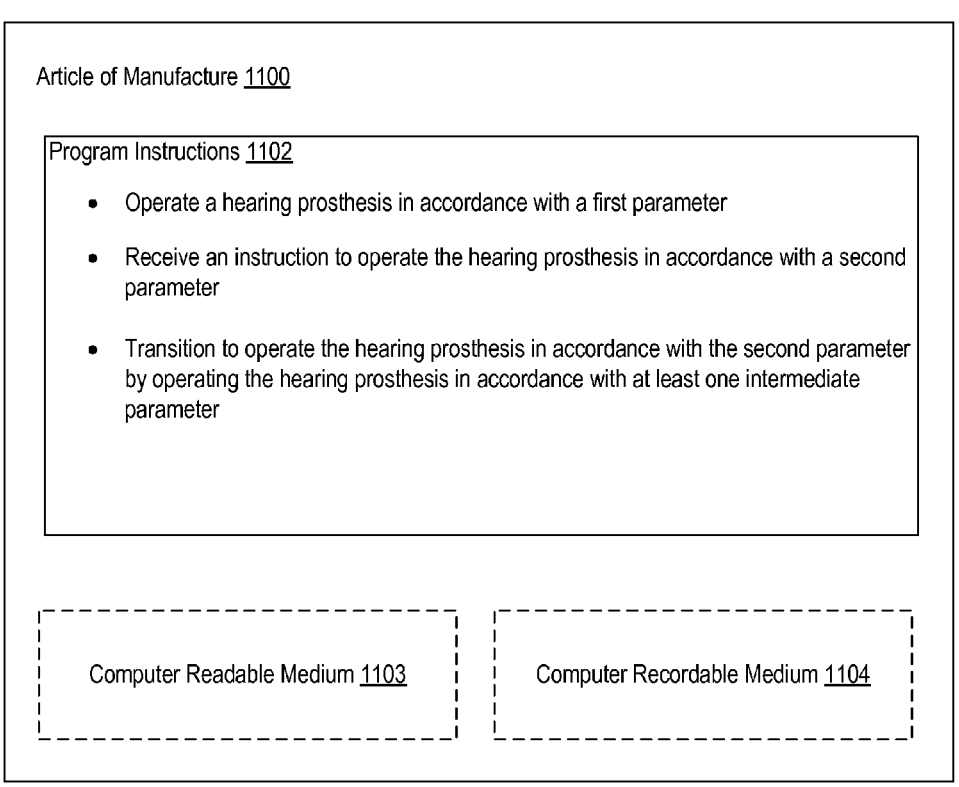
FIG. 11 depicts an article of manufacture including computer readable media with instructions for executing functions, in accordance with one embodiment.

FIG. 11 shows a schematic illustrating a conceptual partial view of an example article of manufacture 1100 that includes program instructions 1102 for executing a process on a computing device. As shown, the program instructions 1102 are directed to transitioning a hearing prosthesis from operating in accordance with a first parameter to operating in accordance with a second parameter. The article of manufacture 1100 may also include a non-transitory computer-readable medium 1103, such as, but not limited to a memory, a hard disk, a DVD, etc., and/or a non-transitory computer-recordable medium 1104, such as, but not limited to, a hard disk drive, a Compact Disc (CD), a Digital Video Disk (DVD), a digital tape, flash memory, etc.

The one or more programming instructions 1102 may be, for example, computer executable and/or logic implemented instructions. In some embodiments, sound processing unit 222 of hearing prosthesis 200 alone or in combination with one or more other processors associated with the hearing prosthesis 200 is configured to perform various operations, functions, or actions to implement the features and functionality of the disclosed systems and methods based, at least in part, on the programming instructions 1102.

Certain aspects of the disclosed systems, methods, and articles of manufacture were described herein with reference to single prosthesis implementations. However, the disclosed systems, methods, and articles of manufacture are equally applicable to binaural hearing prosthesis implementations (i.e., implementations in which a hearing prosthesis recipient has two (or more) hearing prostheses positioned in the same or different ears). In such implementations, one hearing prosthesis may engage in one type of transition while another hearing prosthesis may engage in the same or another type of transition, or no transition at all.

Moreover, as described above, aspects of the disclosed systems, methods, and articles of manufacture described herein are generally applicable to any type of medical stimulation prosthesis, including prosthetic-limb stimulation devices, vibration-based hearing devices, direct acoustic stimulation devices, auditory brain stem implants, or any other type of medical stimulation prosthesis that employs a particular stimulation strategy or a number of changeable stimulation parameters.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method comprising:
a sound processor operating a hearing prosthesis in accordance with a first operation strategy;
the sound processor receiving an instruction to operate the hearing prosthesis in accordance with a second operation strategy;
in response to the receiving, the sound processor transitioning to operate the hearing prosthesis in accordance with a third operation strategy, the third operation strategy being characterized by:
the sound processor alternating between periods of (i) operating the hearing prosthesis in accordance with the first operation strategy, and (ii) operating the hearing prosthesis in accordance with the second operation strategy; and
while the sound processor is alternating between the periods of (i) operating the hearing prosthesis in accordance with the first operation strategy, and (ii) operating the hearing prosthesis in accordance with the second operation strategy, the sound processor increasing an amount of time in which the sound processor is operating the hearing prosthesis in accordance with the second operation strategy.

2. The method of claim 1, wherein the sound processor alternating between the periods comprises the sound processor alternating between the periods at substantially regular intervals.

3. The method of claim 1, wherein the sound processor alternating between the periods comprises the sound processor alternating between the periods at substantially non-regular intervals.

4. The method of claim 1, wherein the sound processor increasing an amount of time in which the sound processor is operating the hearing prosthesis in accordance with the second operation strategy comprises:
the sound processor intermittently increasing a length of each period of time in which the sound processor is operating the hearing prosthesis in accordance with the second operation strategy; and
the sound processor intermittently decreasing a length of each period of time in which the sound processor is operating the hearing prosthesis in accordance with the first operation strategy.

5. The method of claim 1, wherein the sound processor alternating between periods of (i) operating the hearing prosthesis in accordance with the first operation strategy, and (ii) operating the hearing prosthesis in accordance with the second operation strategy comprises:
the sound processor alternating between periods of (a) operating the hearing prosthesis in accordance with the first operation strategy, and (b) operating the hearing prosthesis in accordance with an intermediate operation strategy;

the sound processor intermittently increasing an amount of time in which the sound processor is operating the hearing prosthesis in accordance with the intermediate operation strategy; and the sound processor alternating between periods of (c) operating the hearing prosthesis in accordance with the intermediate strategy, and (d) operating the hearing prosthesis in accordance with the second operation strategy.

6. A method comprising:
a sound processor operating a hearing prosthesis in accordance with a first operation strategy;
the sound processor receiving an instruction to operate the hearing prosthesis in accordance with a second operation strategy;
in response to the receiving, the sound processor transitioning to operate the hearing prosthesis in accordance with a third operation strategy, the third operation strategy being characterized by:
the sound processor alternating between periods of (i) operating the hearing prosthesis in accordance with the first operation strategy, and (ii) operating the hearing prosthesis in accordance with the second operation strategy;
the sound processor increasing a loudness associated with the second operation strategy; and
the sound processor decreasing a loudness associated with the first operation strategy.

7. The method of claim 6, wherein the period of operating the hearing prosthesis in accordance with the first operation strategy and the period of operating the hearing prosthesis in accordance with the second operation strategy are about equal in length.

8. The method of claim 6, wherein the third operation strategy is further characterized by:
the sound processor increasing an amount of time in which the sound processor is operating the hearing prosthesis in accordance with the second operation strategy.

9. The method of claim 8, wherein the sound processor increasing an amount of time in which the sound processor is operating the hearing prosthesis in accordance with the second operation strategy comprises:
the sound processor increasing a length of each period of time in which the sound processor is operating the hearing prosthesis in accordance with the second operation strategy; and
the sound processor decreasing a length of each period of time in which the sound processor is operating the hearing prosthesis in accordance with the first operation strategy.

10. The method of claim 8, wherein the sound processor alternating between periods of (i) operating the hearing prosthesis in accordance with the first operation strategy, and (ii) operating the hearing prosthesis in accordance with the second operation strategy comprises:
the sound processor alternating between periods of (a) operating the hearing prosthesis in accordance with the first operation strategy, and (b) operating the hearing prosthesis in accordance with an intermediate operation strategy;
the sound processor increasing an amount of time in which the sound processor is operating the hearing prosthesis in accordance with the intermediate operation strategy; and
the sound processor alternating between periods of (c) operating the hearing prosthesis in accordance with the intermediate strategy, and (d) operating the hearing prosthesis in accordance with the second operation strategy.

11. The method of claim 6, wherein the sound processor alternating between the periods comprises the sound processor alternating between the periods at substantially regular intervals.

12. The method of claim 6, wherein the sound processor alternating between the periods comprises the sound processor alternating between the periods at substantially non-regular intervals.

13. The method of claim 6,
wherein the sound processor increasing a loudness associated with the second strategy comprises the sound processor increasing a loudness associated with the second strategy in accordance with a substantially-linearly increasing function, and
wherein the sound processor decreasing a loudness associated with the first strategy comprises the sound processor decreasing a loudness associated with the first strategy in accordance with a substantially-linearly decreasing function.

14. The method of claim 6,
wherein the sound processor increasing a loudness associated with the second strategy comprises the sound processor increasing a loudness associated with the second strategy in accordance with a substantially-non-linearly increasing function, and
wherein the sound processor decreasing a loudness associated with the first strategy comprises the sound processor decreasing a loudness associated with the first strategy in accordance with a substantially-non-linearly decreasing function.

* * * * *